United States Patent [19]
Miyaji et al.

[11] Patent Number: 4,983,725
[45] Date of Patent: Jan. 8, 1991

[54] MANNOBIOSE DERIVATIVES

[75] Inventors: Hideki Miyaji, Inazawa; Shusaburo Hokukoku, Kani; Munehiro Tomikawa, Chiba; Sadao Hirota, Chigasaki; Hiroshi Kikuchi, Tokyo, all of Japan

[73] Assignees: Meito Sangyo Co., Ltd., Nagoya; Daiichi Seiyaku Co., Ltd., Tokyo, both of Japan

[21] Appl. No.: 176,329

[22] Filed: Mar. 31, 1988

[30] Foreign Application Priority Data

Apr. 3, 1987 [JP] Japan .................... 62-82736

[51] Int. Cl.$^5$ .................... C07H 3/04; C07H 5/04
[52] U.S. Cl. .................... 536/4.1; 536/18.2; 536/22; 536/53
[58] Field of Search .................... 536/4.1, 18.2, 22, 53; 436/829

[56] References Cited

U.S. PATENT DOCUMENTS

| | | | |
|---|---|---|---|
| 2,504,983 | 4/1950 | Isbell et al. | 536/53 |
| 2,802,819 | 8/1957 | Lederer et al. | 536/18.2 |
| 3,142,620 | 7/1964 | Bloch | 536/18.2 |
| 4,603,044 | 7/1986 | Geho et al. | 436/829 |

FOREIGN PATENT DOCUMENTS

| | | |
|---|---|---|
| 0155625 | 9/1985 | European Pat. Off. |
| 57-72996 | 5/1982 | Japan |
| 57-72997 | 5/1982 | Japan |
| 57-146797 | 9/1982 | Japan |
| 62-209092 | 9/1987 | Japan |

OTHER PUBLICATIONS

Nakajima et al; J. Biol. Chem., 249 (23):7679-7684 (1974).
Ghosh et al; Biochim. Biophys. Acta, 632:562-572 (1980).
Wu et al; Biochim. Biophys. Acta, 675:19-29 (1981).
Szoka, Jr. et al; Biochem. Biophys. Res. Commun., 110(1):140-146 (1983).
Ogawa et al; Carb. Res., 104:271-283 (1982).

Primary Examiner—Ronald W. Griffin
Assistant Examiner—Nancy S. Carson
Attorney, Agent, or Firm—Burns, Doane, Swecker & Mathis

[57] ABSTRACT

Novel mannobiose derivative represented by the general formula [I]:

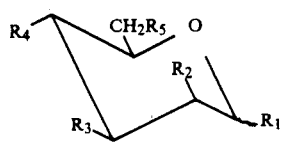

wherein groups of $R_1$ to $R_5$ each represents —OH, —OR$_6$, —NHR$_6$, (R$_6$ represents an acyl group) or a group represented by the following formula (a), (b), (c), (d) or (e), provided that one of $R_1$ to $R_5$ represents —OR$_6$ or —NHR$_6$, one of the other 4 groups of $R_1$ to $R_5$ represents one of the groups represented by the formulae (a) to (e), and the remaining 3 groups of $R_1$ to $R_5$ represent —OH:

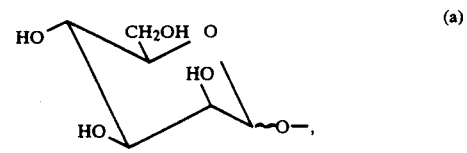

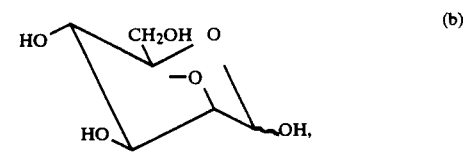

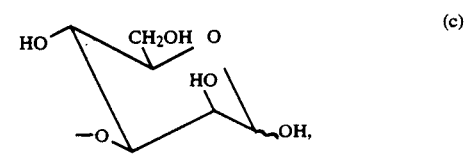

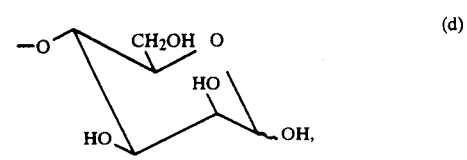

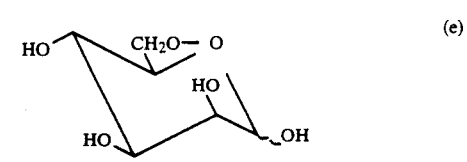

wherein represents α or β bond are provided by the invention.

These compounds give liposomes a specific affinity for Kupffer cells of liver, and can be produced industrially.

7 Claims, No Drawings

MANNOBIOSE DERIVATIVES

BACKGROUND OF THE INVENTION

(1) Field of the Invention

This invention relates to novel mannobiose derivatives useful as a component modifying pharmaceutical preparations, such as liposomes, having a specific affinity for Kupffer cells of liver.

(2) Prior Art

Recently, organ- or cell-directed preparations have been reported in the pharmaceutical and medical fields. For example, several proposals have been made regarding a technique that a drug is selectively delivered to an objective internal organ or cells by administering the drug encapsulated in liposomes.

One such proposal is found in a report by Szoka, et al. (Biochem. Biophys. Res. Comm., 110, 140–146 (1983)) relating to a liposomal preparation of which target is macrophage cells such as Kupffer cells of the liver. In this prior art, a fatty acid diester of dimannosylglceride is mixed with liposomal lipid membrane to give the liposomes an affinity for macrophage cells, but the above diester compound is a natural substance isolated from a luteus coccus, so it is difficult to produce the compound industrially. Further, as examples of research using a synthetic substance as a liposome lipid membrane-modifying substance for targeting macrophage cells, typically Kupffer cells of liver, a report by Bachhawat et al. (Biochim. cells of liver, a report by Shen et al. (Biochim. Biophys. Acta, 632, 562–572 (1980)), a report by Shen et. al. (Biochim. Biophys. Acta, 674, 19–29 (1981)), are shown. In the former, a substance obtained by coupling (i) p-aminophenyl-D-mannoside obtained by reduction of p-nitrophenyl-D-mannoside, (ii) phosphatidylethanolamine which is too expensive to obtain as a pure product among natural phospholipids and (iii) glutaraldehyde is used. In the latter report, a compound obtained by linking a hexyl group (—(CH$_2$)$_6$—) to a hydroxyl group at the 3-position of cholesterol and further linking the resulting hexyl group to the C1-position of D-mannose through thio group (—S—) is used. Thus, in both methods, compounds having a complicated structure are used and are not useful in view of industrial production, safety after administration to living bodies or the like.

As is seen from the foregoing, though liposomal preparations of which target is macrophage cells, typically Kupffer cells of the liver, have been prepared, the objective efficiency for the targetting and industrial production have not been attained.

SUMMARY OF THE INVENTION

The primary object of this invention is to provide novel substances capable of giving liposome an effective and specific affinity for Kupffer cells of liver, and capable of being produced industrially.

The objective compound of this invention is represented by the general formula [I]:

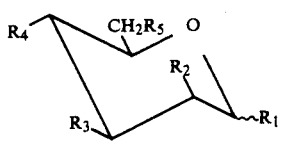

[I]

wherein groups of R$_1$ to R$_5$ each represents —OH, —OR$_6$, —NHR$_6$, (R$_6$ represents an acyl group) or a group represented by the following formula (a), (b), (c), (d) or (e), provided that one of R$_1$ to R$_5$ represents —OR$_6$ or —NHR$_6$, one of the other 4 groups of R$_1$ to R$_5$ represents one of the groups represented by the formulae (a) to (e), and the remaining 3 groups of R$_1$ to R$_5$ represent —OH:

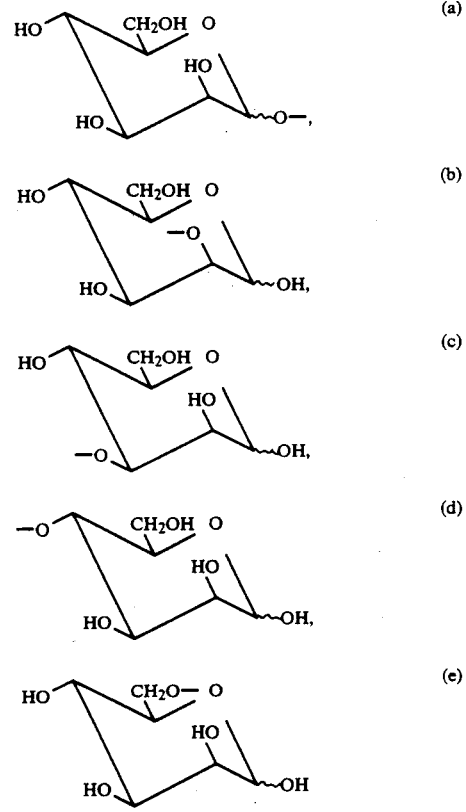

wherein ⁓⁓⁓ represents α or β bond. Liposomes containing a mannobiose derivative of the general formula [I] in its membrane have satisfactorily a specific affinity for the objective cells.

DESCRIPTION OF THE PREFERRED EMBODIMENTS

The group represented by the formula (a) is preferable among the groups represented by the formulae (a) to (e), and among the compounds represented by the formula [I], the compound represented by formula [I] wherein R$_3$, R$_4$ or R$_5$ is the group represented by the formula (a) are preferable.

An acyl group having 12 to 30 carbon atoms may preferably be used as the acyl group in the definition of R$_6$, and examples thereof include straight or branched, or saturated or unsaturated acyl groups such as dodecanoyl, tridecanoyl, tetradecanoyl, pentadecanoyl, hexadecanoyl, heptadecanoyl, octadecanoyl, nonadecanoyl, eicosanoyl, heneicosanoyl, docosanoyl, tricosanoyl, tetracosanoyl, hexacosanoyl, triacontanoyl, 9-hexadecenoyl, 9-octadecenoyl, 9,12-octadecadienoyl, 9,12,15-octadecatrienoyl, 11-eicosenoyl, 11,14-eicosadienoyl, 11,14,17-eicosatrienoyl, 4,8,12,16-eicosatetraenoyl, 13-docosenoyl, 4,8,12,15,19-docosapentaenoyl, 15-tetracosenoyl, 2-decanylhexadecanoyl, 2-tetradecylhexadecanoyl, 2-tetradecylhexadecenoyl and 2-tetradecenylhexadecanoyl. Eicosanoyl is preferable among them.

Further, the position to which —NHR$_6$ or —OR$_6$ is linked in the formula [I] is not specifically limited, but it is generally desirable that R$_1$ represents —NHR$_6$ or —OR$_6$.

Methods for preparing the mannobiose derivatives represented by the formula [I] are described below.

Compounds of the formula [I] wherein one of R$_1$ to R$_5$ represents —OR$_6$ and compounds of the formula [I] wherein one of R$_1$ to R$_5$ represents —NHR$_6$ are prepared by different methods. Each method is described in detail below.

(1) When one of R$_1$ to R$_5$ represents —OR$_6$:

Mannobiose, wherein 2 mannoses are linked together, can be used as starting material. Examples of mannobiose include mannopyrasylmannopyranose, etc. such as α-1,6-mannobiose obtained from yeasts, α-1,3-mannobiose obtained from a kind of mushroom and β-1,4-mannobiose. The objective compound can be obtained by reacting one of the above mannobioses with R$_6$COX (wherein X means a halogen atom) or (R$_6$CO)$_2$O in an aqueous solvent or a nonaqueous solvent.

When the above reaction is carried out in an aqueous solvent, R$_6$COX or (R$_6$CO)$_2$O may be added into an aqueous solution containing about 20 to 90% of mannobiose while the pH of the solution is maintained at about 9.0 with an alkali such as sodium hydroxide or potassium hydroxide. R$_6$COX or (R$_6$CO)$_2$O is usually used in an amount of 0.1 to 1 times the molar amount of mannobiose. The reaction is usually carried out at 0 to 60° C., preferably 40 to 50° C. for about 1 to 5 hours.

When the above reaction is carried out in a nonaqueous solvent, R$_6$COX or (R$_6$CO)hd 2O may be reacted with the mannobiose in the presence of a base in a mixture of (1) a solvent such as acetone, dioxane, chlorobenzene, toluene, ethyl acetate or methylene chloride and (2) a solvent such as hexamethylphosphoric triamide (hereinafter referred to as HMPA) or dimethylsulfoxide. A mixture of toluene and HMPA is preferable among them. The above base includes an organic base such as pyridine, 4-dimethylaminopyridine, or triethylamine and an inorganic base such as sodium hydroxide, pottasium hydroxide, sodium carbonate, potassium carbonate or sodium bicarbonate, preferably pyridine. R$_6$COX or (R$_6$CO)$_2$O is usually used in an amount of 0.2 to 4.0 times, preferably 1.0 to 2.0 times, the molar amount of mannobiose. The base is usually used in an equimolar cr molar excess amount to the amount of R$_6$COX or (R$_6$CO)$_2$O. The reaction is usually carried out at 60 to 100° C., preferably at 70 to 90° C. for 2 to 6 hours.

When the product is a mixture of mannobiose monofatty acid esters wherein linking positions of the fatty acid ester are different, it can be used without separating to prepare the objective liposome preparation. Usually, the mixture is separated by separating method such as column chromatography to obtain a mannobiose monofatty acid ester in the form of single component.

The method of Roulleau et al. (Tetrahedron Letters 24, 719-722 (1983)) may be used in order to selectively link an acyl group to the hydroxyl group at the 1-position of the reducing end mannose of mannobiose to form an ester bond. That is, a mannobiose monofatty acid ester wherein the acyl group, is linked to the hydroxyl group at the C1-position of the reducing end mannose of mannobiose may be prepared by reacting (i) a reactive acylating agent such as an amide compound obtained by reaction of a desired R$_6$COOH with thiazolidinethione or an ester compound obtained by reaction of the R$_6$COOH with p-nitropherol, mercaptobenzothiazole, 8-hydroxyguinoline or the like, for example N-eicosanoylthiazolidinethione, p-nitrophenyl eicosanoate, mercaptobenzothiazolyl eicosanoate, 8-eicosanoyl-oxyquinoline or the like, with (ii) a mannobiose (excluding α-D-mannopyranosyl-α-D-mannopyranoside and α-D-mannopyranosyl-β-D-mannopyranoside) in the presence of a base. Examples of the base used in the reaction include potassium hydride, sodium hydride, etc., preferably sodium hydride. Amount of the base is, preferably 0.8 to 1.2 times the molar amount of the acylating agent. Preferred examples of a reaction solvent include pyridine, methylpyrrolidone, dimethylsulfoxide, hexamethylphosphoric triamide, etc. The amount of the reaction solvent is not particularly limited, may be 5 to 50 times the amount of mannobiose. Further, the amount of the acylating agent may be 0.1 to 1.0 times, preferably 0.2 to 0.5 times the molar amount of mannobiose. When the acylating agent is ar amide compound obtained by reaction of R$_6$COOH with thiazolidinethione or an ester compound obtained by reaction of R$_6$COOH with mercaptobenzothiazole, 8-hydroxyquinoline or the like, the reaction may be carried out at 10 to 60° C., preferably 20 to 40° C. for about 1 to 5 hours. When the acylating agent is an ester compound obtained by reaction of R$_6$COOH with p-nitrophenol, the reaction may be carried out at 40 to 90° C., preferably 60 to 80° C. for 1 to 5 hours.

(2) When one of R$_1$ to R$_5$ is —NHR$_6$:

Hydroxyl groups of mannobiose as a starting compound are protected by proper protective groups such as a benzylidene group and an acetyl group, and then a hydroxyl group is replaced by an amino group at a desired position of the resulting compound according to a known method. The resulting compound is reacted with R$_6$COOH in the presence of a condensing agent in a proper organic solvent to link the acyl group to the amino group. Examples of the solvent include tetrahydrofuran, dimethylformamide, dichloromethane, ethyl acetate, methanol, ethanol, benzene, and a mixture thereof, and the like. The amount of the solvent is not particularly limited, and may be 10 to 100 times the weight of the starting compound. Examples of the condensingagent include N,N'-dicyclohexylcarbodiimide (DCC), N-ethyl-5-phenylisoxazolium-3'-sulfonate, diphenylketene-p-tolylimine, 1-ethoxycarbonyl-2-ethoxy-1,2-dihydroquinoline (EEDQ), N-isobutyloxycarbonyl-2-isobutyloxy-1,2-dihydroquinoline (IIDQ), diethylphosphorocyanidate (DEPC), and so on. The amount of the condensing agent may properly be selected and varied, and for example, may be 1 to 3 moles per 1 mole of the starting compound. Further, the amount of R$_6$COOH may be 1 to 3 moles per 1 mole of the starting compound. The reaction may be carried out at −10 to 50° C., preferably at 0 to 30° C. for 2 to 72 hours.

The resulting compound may be treated with an alkali such as sodium alkoxide (e.g., sodium methoxide), ammonia or triethylamine in a polar solvent such as, methanol or ethanol or in a mixture thereof, or a mixture of the above solvent and chloroform to prepare a desired compound. The reaction may be carried out at 0 to 40° C. for 1 to 10 hours.

After the reaction, the objective compound may, if necessary, be separated and purified by utilizing known separating and purifying methods such as removal of solvent, crystallization and column chromatography.

A compound wherein the hydroxyl group at the C1-position of the reducing end mannose of mannobiose is replaced by an acylamino group may be prepared in the following manner. Hydroxyl groups of mannobiose are protected with acetyl groups, and the acetyloxy group at the C1-position of the reducing end mannose of mannobiose is replaced by a bromine atom. The resulting compound is then reacted with an azide salt to replace the bromine atom by an azido group, followed by reduction to obtain a mannobiosylamine wherein the hydroxyl group at the C1-position of the reducing end mannose of mannobiose is replaced by an amino group. An acyl group is linked to the amino group using the above active ester method, and then the protective groups bonding to the hydroxyl groups other than that of the desired position are removed using an alkali such as sodium methoxide to prepare the objective N-acyl-mannobiosylamine wherein the hydroxyl group at the C1-position of the reducing end mannose of mannobiose is replaced by an acylamino group.

Further, a compound wherein the hydroxyl group at the C2-position of the reducing mannose or the nonreducing end mannose of mannobiose is replaced by an acylamino group may be prepared as follows. That is, mannosamine and mannose are condensed using a known condensing reaction, and the resulting mannopyranosyl-mannosamine or 2-deoxy-2-amino-mannopyranosylmannopyranose is reacted with $R_6COOH$ using the above active ester method to obtain the objective compound.

Next, a method for preparing a liposome which contains a compound of the invention in liposomal membrane is described below.

An aqueous dispersion of liposomes is prepared using membrane components such as a phospholipid (e.g., phosphatidylcholine, sphingomyelin or phosphatidylethanolamine), a glycolipid, a dialkyl (double-chain) amphiphiles according to a known method (Annual Review of Biophysics and Bioengineering, 9, 467–508 (1980)). The liposomes may further contain a membrane stabilizer such as a sterol (e.g., chlesterol or chlestanol), a charged modifier such as a dialkyl phosphate, a diacylphosphatidic acid or stearylamine, and an antioxidant such as α-tocopherol in the membrane. An aqueous solution of a compound of the formula [I] is added to the thus prepared aqueous dispersion of liposomes, and the mixture is allowed to stand for a certain time, preferably under warming to or above the phase transition temperature of the membrane, or above 40° C., and then allowed to cool to prepare objective liposomes. The liposomes may also be prepared by mixing a compound of the formula [I] with membrane components, and treating the mixture according to a known method to prepare the liposomes.

In order to give the liposome an affinity for the aforesaid Kupffer cells of liver, it is preferable that the ratio of the compound of the invention to the total lipid membrane components is about 1/40 mole ratio or more in a preparation step thereof.

Liposomes containing a compound of the invention in its membrane have a specific affinity for not only Kupffer cells of the liver but also macrophages, monocytes, spleen cells, lymphocytes and aleolar macrophages. Therefore, the compounds of the invention are important as a component modifying liposomes.

Further, the compounds of the invention may give such affinity not only to the liposomes but also to micells and microemulsions.

The invention is further described below according to examples, but should not be interpreted to be limited thereto.

EXAMPLE 1

400 mg of 2-O-α-D-mannopyranosyl-D-mannopyranose was dissolved in 1 ml of water, and an aqueous 10% sodium hydroxide solution was added thereto to adjust the pH to 9.0. Then, 277 mg of arachidyl chloride prepared from arachidic acid and thionyl chloride was added by portions at 50° C. while the reaction pH was maintained at 9.0 with an aqueous 10% sodium hydroxide solution, and stirred at the same temperature for one hour.

After the reaction, the formed precipitate was collected by filtration and recrystallized from methanol. The resulting crystalline substance was twice purified by silica gel column chromatography (Solvent system; chloroform/methanol =30/1 to 5/1) to obtain a mixture of monoeicosanoic acid esters of 2-O-α-D-mannopyranosyl-D-mannopyranose.

Yield ; 50 mg,

TLC ; Rf value 0.5 or less (mixture) . ($CHCl_3$/MeOH=2/1).

Elementary analysis as $C_{32}H_{60}O_{12}$ (Molecular weight 636.49);,. Calculated(%), C 60.38, H 9.43, 0 30.15, Found(%), C 60.75, H 10.05, 0 29.20.

IR(KBr); 2845, 2910, 1465 (CH), 1730 (—CO—O—)

$^1$H-NMR (90 MHz, $CDCl_3$/TMS); δ0.7–1.40 (39H, Eicosanoyl), 2.8–4.0 (21H, Mannobiose ring protons),

EXAMPLE 2

400 mg of 4-0-8-D-manncpyranosyl-D-mannopyranose was dissolved in 8 ml of hexamethylphosphoric triamide (HMPA), and 8 ml of pyridine was added. Then, 730 mg of arachidyl chloride separately prepared from arachidic acid and thionyl chloride was dissolved in 1.5 ml of toluene, and added to the above reaction solution at 30° C. or less, and stirred at 80 to 85° C. for about 4 hours to conduct the reaction.

After the reaction, the reaction solution was concentrated under reduced pressure, and the resulting syrup was twice purified by silica gel column chromatography (solvent system; chloroform/acetone=30/1 to 5/1) to obtain a mixture of monoeicosanoic acid esters of 4-O-β-D-mannopyranosyl-D-mannopyranose (4 components).

Yield ; 447 mg

TLC ; Rf value 0.5 or less (4 components mixture) ($CHCl_3$/MeOH=2/1)

IR(KBr); 2845, 2910, 1465 (CH), 1730 (—CO—O—)

Elementary analysis as $C_{32}H_{60}O_{12}$ (Molecular weight 636.49), Calculated(%), C 60.38, H 9.43, 0 30.15, Found(%), C 60.50, H 9.94, 0 29.56 .

$^1$H-NMR (90 MHz, $CDCl_3$/TMS); δ0.7–1.40 (39H, Eicosanoyl), 2.8–4.0 (21H, Mannobiose ring protons)

EXAMPLE 3

300 mg of the mixture obtained in Example 2 was fractionated by silica gel chromatography (Solvent system; chloroform/methanol 10/1 to 7/1), followed by powdering from chloroform/methanol (1/1) and ether to obtain 4-O-(6-O-eicosanoyl-β-D-mannopyranosyl)-D-mannopyranose wherein eicosanoic acid is linked to the hydroxyl group at the $C_6'$-position by ester bond.

Yield ; 126 mg.
Decomposition point; 152–158° C..
TLC ; Rf=0.50 (CHCl$_3$/MeOH=2/1).
IR(KBr); 2845, 2910, 1465 (CH), 1730 (—CO—O—).
Elementary analysis as C$_{32}$H$_{60}$O$_{12}$ (Molecular weight 636.49); Calculated(%), C 60.38, H 9.43, 0 30.15, Found(%), C 60.28, H 9.82, 0 29.90 .

$^1$H-NMR (90 MHz, DMSO-d$_6$/TMS);δ0.7–1.40 (39H, Eicosanoyl), 2.8–4.0 (21H, Mannobiose ring protons).

$^{13}$C-NMR (90 MHz, DMSO-d6/TMS); δ173.0, 100.9, 100.8, 938, 77.9, 74.2, 73.2,-71.0, 70.6, 70.4, 69.0, 66.9, 63.7, 60.6.

EXAMPLE 4

After elution of 4-O-(6-O-eicosanoyl-δ-D-mannopyranosyl)-D-mannopyranose of Example 3, elution was further continued with chloroform/methanol (5/1 to 1/1) to obtain a mixture of 6-O-eicosanoyl-4-O-δ-1-mannopyranosyl-D-mannopyranose, 4-O-(3-O-eicosanoyl-δ-D-mannopyranosyl)-D-mannopyranose and 2-O-eicosanoyl-4-O-δ-D-mannopyranosyl-D-mannopyranose wherein an eicosanoic acid is linked to the hydroxyl group at the C$_6$-, C$_3'$- and C$_2$-positions, respectively.
Yield ; 108 mg.
Decomposition point; 148–152° C.
TLC ; Rf=0.12 (3 components) (CHCl$_3$/MeOH=2/1).
IR(KBr); 2845, 2910, 1465 (CH), 1730 (—CO—0—)
Elementary analysis as C$_{32}$H$_{60}$O$_{12}$ (Molecular weight 636.49);, Calculated(%), C 60.38, H 9.43, 0 30.15, Found(%), C 60.67, H 9 73, 0 29.60.

$^1$H-NMR (90 MHz, DMSO-d6/TMS); δ0.7–1.40 (39H, Eicosanoyl), 2.8–4.0 (Mannobiose ring protons).

$^{13}$C-NMR (90 MHz, DMSO-d$_6$/TMS); δ173.0, 172.9, 172.8, 103.1, 102.6, 96.4, 81.4, 79.1, 77.4, 74.3, 73.6, 73.3, 71.1, 70.7, 70.5, 70.3, 69.1, 67.5, 67.0, 65.1, 63.9, 63.7, 61.1, 61.0.

EXAMPLE 5

300 mg of 4-O-δ-D-mannopyranosyl-D-mannopyranose was dissolved in 6 ml of HMPA, and 6 ml of pyridine was added thereto. Separately, 365 mg of myristoyl chloride prepared from myristic acid and thionyl chloride was dissolved in 1 ml of toluene, and the solution was added to the above reaction solution at 30° C. or less, and the mixture was subjected to reaction at 80 to 85° C. for 4 hours with stirring. After the reaction, the reaction solution was concentrated under reduced pressure, and the resulting syrup was twice purified by silica gel chromatography (Solvent system; chloroform/methanol=30/1 to 5/1) to obtain a mixture of monomyristic acid esters of 4-O-δ-D-mannopyranosyl-D-mannopyranose.
Yield ; 237 mg.
TLC ; Rf value 0.48 or less (mixture), (CHCl$_3$/MeOH=2/1).
IR(KBr); 2845, 2910, 1465 (CH), 1730 (—CO—O—).
Elementary analysis as C$_{26}$H$_{48}$O$_{12}$ (Molecular weight 552.43); Calculated(%), C 56.52, H 8.69, 0 34.73 Found(%) , C 56.74, H 9.97, 0 33.29.

$^1$H-NMR (90 MHz, CDCl$_3$/TMS); δ0.7–1.40 (27H, Myristoyl), 2.8–4.0 (Mannobiose ring protons).

EXAMPLE 6

150 mg of the mixture of monomyristic acid esters of mannobiose obtained in Example 5 was further twice fractionated by silica gel chromatography (Solvent system; chloroform/methanol=5/1 to 3/1) to obtain 6-O-myristoyl-4-O-δ-D-mannopyranosyl-D-mannopyranose wherein myristic acid is linked to the hydroxyl group at the C$_6$-position by ester bond.
Yield ; 32 mg.
TLC ; Rf value 0.15 (CHCl$_3$/MeOH=2/1).
IR(KBr); 2845, 2910, 1465 (CH), 1730 (—CO—O—).
Elementary analysis as C$_{26}$H$_{48}$O$_{12}$ (Molecular weight 552.43); Calculated(%), C 56.52, H 8.69, 0 34.73, Found(%), C 56.22, H 9.01, 0 34.77.

$^1$H-NMR (90 MHz, CDCl$_3$/TMS); δ0.7–1.40 (27H, Myristoyl), 2.8–4.0 (Mannobiose ring protons).

$^{13}$C-NMR (90 MHz, DMSO-d$_6$/TMS); δ173.1, 100.9, 95.8, 92.4, 77.7, 77.4, 73.6, 70.7, 70.6, 70.1, 69.1, 67.0, 63.5, 61.4.

EXAMPLE 7

The procedure in Example 5 was repeated using 449 mg of stearoyl chloride in place of 365 mg of myristoyl chloride to obtain a mixture of monostearic acid esters of 4-O-δ-D-mannopyranosyl-D-mannopyranose.
Yield ; 267 mg.
TLC ; Rf value 0.51 or less (mixture) (CHCl$_3$/MeOH=2/1).
IR(KBr); 2845, 2910, 1465 (CH), 1730 (—CO—O—).
Elementary analysis as C$_{30}$H$_{56}$O$_{12}$ (Molecular weight 608.47); Calculated(%), C 59.21, H 9.20, 0 31.53, Found(%), C 59.11, H 9.11, 0 31.78.

$^1$H-NMR (90 MHz, CDCl$_3$/TMS); δ0.7–1.4 (35H, Stearoyl), 2.8–4.0 (Mannobiose ring protons).

EXAMPLE 8

The procedure of Example 5 was repeated using 530 mg of behenoyl chloride in place of 365 mg of myristoyl chloride to obtain a mixture of monobehenic acid esters of 4-O-δ-D-mannopyranosyl-D-mannopyranose.
Yield ; 262 mg.
TLC ; Rf value 0.51 or less (mixture) (CHCl$_3$/MeOH=2/1).
IR(KBr); 2845, 2910, 1465 (CH), 1730 (—CO—O—).
Elementary analysis as C$_{34}$H$_{64}$O$_{12}$ (Molecular weight 664.51); Calculated(%), C 61.45, H 9.63, 0 28.88, Found(%), C 61.30, H 9.99, 0 28.71.

$^1$H-NMR (90 MHz, CDCl$_3$/TMS); δ0.7–1.41 (43H, Behenoyl), 2.8–4.0 (21H, Mannobiose ring protons).

REFERENCE EXAMPLE 1

4-O-(2,3,4,6-Tetra-O-acetyl-δ-D-mannopyranosyl)-2,3,6-tri-O-acetyl-D-mannopyranosylamine (hereinafter referred to as compound A).

16 ml of pyridine and 10 ml of acetic anhydride were added to 2 g of 4-O-δ-D-mannopyranosyl-D-mannopyranose, and stirred at room temperature overnight. The product was treated in a conventional manner to obtain 3.98 g of 4-O-(2,3,4,6-tetra-O-acetyl-δ-D-manncpyranosyl)-1,2,3,6-tetra-O- acetyl-D-mannopyranose as white powder. This compound was dissolved in 20 ml of dichloromethane, and 20 ml of a hydrogen bromide-saturated acetic acid solution (30%, w/v) was added thereto under ice cooling, followed by stirring at 0° C. for 15 hours. The reaction solution was poured into ice water and extractad with chloroform. The extract was washed successively with ice water and with ice-cooled aqueous sodium bicarbonate, and dried over anhydrous magnesium sulfate. The solution is concentrated to obtain 3.97 g of 4-O-(2,3,4,6-tetra-O-acetyl-δ-D-mannopyranosyl)-2,3,6-tri-O-acetyl-D-mannopyranosyl bromide. Then, 3.97 g of this compound was dissolved in 80 ml of dimethylformamide, and 8.0 g of sodium azide was added, followed by stirring overnight. The reaction mixture was poured into ice water and extracted with chloroform. The extract was washed successively with ice water, 5% aqueous hydrochloric acid and ice-cooled aqueous sodium bicarbonate, and dried to obtain 3.84 g of crude 4-O-(2,3,4,6-tetra-O-acetyl-δ-D-mannopyranosyl)-2,3,6-tri-O-acetyl-D-mannopyranosyl azide. This compound was purified by silica gel chromatography (Solvent system; chloroform/acetone=30/1) to obtain 2.98 g of 4-O-(2,3,4,6-tetra-O-acetyl-δ-D-mannopyranosyl)-2,3,6-tri-O-acetyl-D-mannopyranosyl azide. Then, 2.88 g of this azide compound was dissolved in 140 ml of methanol and subjected to a catalytic reduction in the presence of 300 mg of platinum dioxide for 2.0 hours. The catalyst was removed by filtration using Celite, and the filtrate was concentrated to obtain 2.57 g of amorphous entitled compound A.

TLC; Rf value 0.3 (chloroform:ethanol=19:1).

REFERENCE EXAMPLE 2

N-Eicosanoyl-4-O-(2,3,4,6-tetra-O-acetyl-mannopyranosyl)-2,3,6-tri-O-acetyl-D-mannopyranosylamine.

580 mg of compound A obtained in Reference example 1 was dissolved in 25 ml of ethanol, and a solution of 627 mg of arachidic acid dissolved in 30 ml of benzene was added. Then, 494 mg of N-ethoxycarbonyl-2-ethoxy-1,2-dihidroquinoline (EEDQ) was further added thereto, followed by stirring at room temperature for 48 hours. The reaction solution was cooled, the precipitated unreacted arachidic acid was removed by filtration, and the filtrate was concentrated. The resulting residue was purified by silica gel chromatography (Solvent system; chloroform:acetone (30:1)) to obtain the entitled compound as white powder.

Yield ; 696 mg.

TLC ; Rf value =0.45 (chloroform:acetone =6:1).

$^1$H-NMR (90 MHz, CDCl$_3$/TMS); δ 0.81–1.60 (39H, Eicosanoyl), 1.97–2.20 (21H, all S, OAc x 7) 6.22 (d, 1H, J$_{NH, 1}$ =9Hz, NH).

IR(KBr); 3300 (NH), 1750 (OAc), 1660 (amido I), 1540 (amido II).

Elementary analysis as C$_{46}$H$_{75}$O$_{18}$N (Molecular weight 930.10); Calculated, C 59.40, H 8.13, N 1.51% Found, C 59.60, H 8.25, N 1.39%.

EXAMPLE 9

N-Eicosanoyl-4-O-δ-D-mannopyranosyl-δ-D-mannopyranosylamine 550 mg of the compound obtained in Reference example 2 was dissolved 40 ml of chloroform and 80 ml of methanol, and 40 mg of sodium methylate was added, followed by stirring at room temperature for 6 hours. The resulting precipitate was separated by filtration and thoroughly washed with methanol and ether to obtain the entitled compound.

Yield ; 240 mg.

mp ; 194–200° C.

$^1$H-NMR (90 MHz DMSO-d$_6$/TMS); 0.80–1.50 (39H, Eicosanoyl), 4.60 (d, 1H, J$_{NH, 1}$ =10Hz, NH).

IR(KBr); 3400–3300 (OH, NH), 1650 (amido I), 1530 (amido II).

Elementary analysis as C$_{32}$H$_{61}$O$_{11}$ (Molecular weight 635.83); Calculated, C 60.45, H 9.67, N 2.20% Found, C 60.25, H 9.57, N 2.15%.

REFERENCE EXAMPLE 3

N-Lauroyl-4-O-(2,3,4,6-tetra-O-acetyl-δ-D-mannopyranosyl)-2,3,6-tri-O-acetyl-D-manncpyranosylamine Compound A (390 mg) was treated in the same manner as in Reference example 2 except that 627 mg of arachidic acid was replaced by 270 mg of lauric acid to obtain the entitled compound.

Yield ; 465 mg.

TLC ; Rf value =0.44 (chloroform:acetone=6:1).

$^1$H-NMR (90 MHz, CDCl$_3$/TMS); 0.80–1.60 (23H, Laurcyl) 1.97–2.21 (21H, all S, OAc x 7) 6.22 (d, 1H, J$_{NH, 1}$ =9Hz, NH).

IR(KBr); 3300 (NH), 1750 (OAc), 1660 (amido I), 1540 (amido II).

Elementary analysis as C$_{38}$H$_{59}$O$_{18}$ (Molecular weight 817.87); Calculated, C 55.81, H 7.27, N 1.71% Found, C 55.60, H 7.38, N 1.58%.

EXAMPLE 10

N-Lauroyl-4-O-δ-D-mannopyranosyl-D-mannopyranosylamine 360 mg of the compound as obtained in Reference example 3 was dissolved in 25 ml of anhydrous methanol, 25 mg of sodium methylate was added, and then the same procedure as in Example 9 was conducted to obtain the entitled compound.

Yield ; 158 mg.

$^1$H-NMR (90 MHz, DMSO-d$_6$/TMS); δ0.80–1.50 (23H, Lauroyl) 4.60 (d, 1H, J$_{NH, 1}$ =10Hz, NH).

IR(KBr); 3400–3300 (OH, NH), 1650 (amido I), 1530 (amido II).

Elementary analysis as C$_{24}$H$_{45}$O$_{11}$N (Molecular weight 523.61); Calculated, C 55.05, H 8.66, N 2.68% ., Found, C 54.82, H 8.72, N 2.67%.

REFERENCE EXAMPLE 4

N-Myristoyl-4-O-(2,3,4,6-tetra-O-acetyl-δ-D-mannopyranosyl)-2,3,6-tri-O-acetyl-D-xannopyranosylamine Compound A (390 mg) was treated in the same manner as in Reference example 2 except that 627 mg of arachidic acid was replaced by 315 mg of myristic acid to obtain the entitled compound.

Yield ; 458 mg.

TLC ; Rf value =0.43 (chloroform:acetone=6:1).

$^1$H-NMR (90 MHz, CDCl$_3$/TMS); δ0.80–1.60 (27H, Myristoyl); 1.97–2.22 (21H, all S, OAc x 7) ; 6.22 (d, 1H, J$_{NH, 1}$ =9Hz, NH).

IR(KBr); 3300 (NH), 1750 (OAc), 1665 (amido I), 1540 (amido II).

Elementary analysis as C$_{40}$H$_{63}$O$_{18}$N (Molecular weight 845.93); Calculated, C 56.79, H 7.51, N 1.66% Found, C 56.38, H 7.71, N 1.58%.

EXAMPLE 11

N-Myristoyl-4-O-δ-D-mannopyranosyl-D-mannopyranosylamine 360 mg of the compound obtained in Reference example 4 was dissolved in 25 ml of anhydrous methanol, 25 mg of sodium methylate was added, and then the same procedure as in Example 9 was conducted to obtain the entitled compound.

Yield ; 175 mg.

$^1$H-NMR (90 MHz, DMSO-d$_6$/TMS); δ0.80–1.50 (27H, Myristoyl) 4.60 (d, 1H, J$_{NH, 1}$ =10Hz, NH).

IR(KBr); 3400–3300 (OH, NH), 1650 (amido I), 1530 (amido II).

Elementary analysis as $C_{26}H_{49}O_{11}N$ (Molecular weight 551.67); Calculated, C 56.61, H 8.95, N 2.54% Found, C 56.88, H 8.77, N 2.48%.

REFERENCE EXAMPLE 5

N-Palmitoyl-4-O-(2,3,4,6-tetra-O-acetyl-δ-D-mannopyranosyl)-2,3,6-tri-O-acetyl-D-xannopyranosylamine Compound A (390 mg) was treated in the same manner as in Reference example 2 except that 627 mg of arachidic acid was replaced by 364 mg of palmitic acid to obtain the entitled compound.

Yield ; 480 mg.

TLC ; Rf value =0.45 (chloroform:acetone =6:1).

$^1$H-NMR (90 MHz, CDCl$_3$/TMS); δ0.80–1.60 (31H, Palmitoyl), 1.97–2.22 (21H, all S, OAc x 7), 6.22 (d, 1H, $J_{NH, 1}$ =9Hz, NH).

IR(KBr); 3300 (NH), 1750 (OAc), 1660 (amido I), 1540 (amido II).

Elementary analysis as $C_{42}H_{67}O_{18}N$ (Molecular weight 873.98); Calculated, C 57.72, H 7.73, N 1.60% Found, C 57.82, H 7.32, N 1.68%.

EXAMPLE 12

N-Palmitoyl-4-O-(δ-D-mannopyranosyl)-D-mannopyranosylamine 360 mg of the compound obtained in Reference example 5 was dissolved in 25 ml of anhydrous methanol, 25 mg of sodium methylate was added, and a procedure similar to that in Example 9 was conducted to obtain the entitled compound.

Yield ; 160 mg.

$^1$H-NMR (90 MHz, DMSO-d$_6$/TMS); δ0.80–1.52 (31H, Palmitoyl) 4.60 (d, 1H, $J_{NH, 1}$ =10Hz, NH).

IR(KBr); 3400–3300 (OH, NH), 1650 (amido I), 1530 (amido II).

Elementary analysis as $C_{28}H_{53}O_{11}N$ (Molecular weight 579.72); Calculated, C 58.01, H 9.21, N 2.42% Found, C 58.18, H 9.50, N 2.32%.

REFERENCE EXAMPLE 6

N-Stearoyl-4-O-(2,3,4,6-tetra-O-acetyl-δ-D-mannopyranosyl)-2,3,6-tri-O-acetyl-D-mannopyranosylamine Compound A (390 mg) was treated in the same manner as in Reference example 2 except that 672 mg of arachidic acid was replaced by 383 mg of stearic acid to obtain the entitled compound.

Yield ; 472 mg.

TLC ; Rf value=0.45 (chloroform:acetone=6:1).

$^1$H-NMR (90 MHz, CDCl$_3$/TMS); δ0.80–1.60 (35H, Stearoyl) ; 1.97–2.22 (21H, all S, OAc x 7) 6.22 (d, 1H, $J_{NH, 1}$ =9Hz, NH).

IR(Br); 3300 (NH), 1750 (OAc), 1660 (amido I), 1540 (amido II).

Elementary analysis as $C_{44}H_{71}O_{18}N$ (Molecular weight 902.04); Calculated, C 58.59, H 7.93, N 1.55% Found, C 58.63, H 8.02, N 1.70%.

EXAMPLE 13

N-Stearoyl-4-O-δ-D-mannopyranosyl-D-mannopyranosylamine 360 mg of the compound as obtained in Reference example 6 was dissolved in 25 ml of anhydrous methanol, 25 mg of sodium methylate was added, and then the same procedure as in Example 9 was conducted to obtain the entitled compound.

Yield ; 192 mg.

$^1$H-NMR (90 MHz, DMSO-d$_6$/TMS); δ0.80–1.50 (35H, Stearoyl) 4.60 (d, 1H, $J_{NH, 1}$ =10Hz, NH).

IR(KBr); 3400–3300 (OH, NH), 1650 (amido I), 1530 (amido II).

Elementary analysis as $C_{30}H_{57}O_{11}N$ (Molecular weight 607.78); Calculated, C 59.29, H 9.45, N 2.30% Found, C 59.42, H 9.58, N 2.58%.

REFERENCE EXAMPLE 7

N-Oleoyl-3-O-(2,3,4,6-tetra-O-benzoyl-δ-D-mannopyranosyl)-2,4,6-tri-O-benzoyl-1-deoxy-1-N-oleoyl-D-mannopyranosylamine 3-O-α-D-mannopyranosyl-D-mannopyranose (500 mg) was treated in the same manner as in Reference example 1 except 10 ml of acetic acid was replaced by 3.2 ml of benzoyl chloride to obtain 410 mg of 3-O-(2,3,4,6-tetra-O-benzoyl-α-D-mannopyranosyl)-2,4,6-tri-O-benzoyl-D-mannopyranosylamine.

Then, 410 mg of the amine compound was treated in the same manner as in Reference example 2 except that 627 mg of arachidic acid was replaced by 403 mg of oleic acid to obtain the entitled compound.

Yield ; 380 mg.

TLC ; Rf value=0.43 (chloroform:acetone=6:1);

$^1$H-NMR (90 MHz, CDCl$_3$/TMS); δ0.80–1.60 (33H, Oleoyl) 6.22 (d, 1H, $J_{NH, 1}$ =9Hz, NH) 7.2–8.3 (35H, Bz x 7).

IR(KBr); 3300 (NH), 1750 (OBz), 1660 (amido I), 1540 (amido II).

Elementary analysis as $C_{81}H_{89}O_{18}N$ (Molecular weight 1364.59); Calculated, C 71.30, H 6.57, N 1.03% Found, C 71.12, H 6.87, N 0.98%.

EXAMPLE 14

N-Oleoyl-3-O-α-D-mannopyranosyl-D-mannopyranosylamine

The compound (360 mg) as obtained in Reference example 7 was dissolved in 25 ml of anhydrous methanol, 25 mg of sodium methylate was added, and then the same procedure as in Example 9 was conducted to obtain the entitled compound.

Yield ; 102 mg.

$^1$H-NMR (90 MHz, DMSO-d$_6$/TMS); δ0.80–1.50 (33H, Oleoyl) 4.60 (d, 1H, $J_{NH, 1}$ =10Hz, NH).

IR(KBr); 3400–3300 (OH, NH), 1650 (amido I), 1535 (amido II).

Elementary analysis as $C_{30}H_{55}O_{11}N$ (Molecular weight 605.76); Calculated, C 59.48, H 9.15, N 2.31% Found, C 59.62, H 9.43, N 2.22%.

EXAMPLE 15

(1) Preparation of liposomes I (containing a compound of the invention)

First, 8.8 μmol of yolk phosphatidylcholine, 5.6 μmol of cholesterol, 0.8 μmol of dicetyl phosphate, and 0.8 μmol or 1.6 mol of one of the mannobiose derivatives of the invention as shown below were dissolved in a mixture of chloroform and methanol (volume ratio 2:1) in a test tube with warming. Then, the organic solvents were removed by a nitrogen gas stream to form a lipid film on the glass wall of the test tube. Then, 3.2 ml of phosphate-buffered physiological saline (pH 7.4, hereinafter abbreviated as PBS) was added thereto, and the mixture was shaken and then subjected to mild ultrasonication to prepare a liposome suspension. The suspension was warmed to 40 to 45° C. and entruded through a polycarbonate membrane filter having a pore size of 0.2 μm to prepare a suspension of liposomes having a particle size of 0.2 μm or less. Then, 1 ml of the suspension was subjected to gel filtration chromatography (Column: Sepharose CL-4B, 1.5 cmφ×15 cm, eluting solution: PBS (pH 7.4)) to further obtain 6.5 ml of a fraction as a liposome fraction which was eluted in the void volume. The lipid in this liposome fraction was quantitatively determined by an enzymatic method using the choline group of yolk phosphatidylcholine as a marker, and the liposome fraction was diluted with PBS (pH 7.4) so that the concentration of total lipids therein became 0.5 μmol/ml. The obtained liposomes and the used mannobiose derivatives is shown below.

| Liposome No. | Mannobiose derivative | Used amount |
| --- | --- | --- |
| I-1 | Compound of Example 3 | 1.6 μmol |
| I-2 | Compound of Example 4 | 0.8 μmol |
| I-3 | Compound of Example 4 | 1.6 μmol |
| I-4 | Compound of Example 9 | 0.8 μmol |
| I-5 | Compound of Example 9 | 1.6 μmol |

(2) Preparation of liposomes II (control)

The same treatment as in the above item (1) was conducted except that 8.8 u mol of yolk phosphatidylcholine, 5.6 μmol of cholesterol and 0.8 μmol of dicetyl phosphate were dissolved in a mixture of chloroform and methanol and the amount of PBS (pH 7.4) to be added to the lipid film was 2.88 ml to obtain 6.2 ml of liposome fraction after gel filtration per 1 ml of the liposome suspension. The whole fraction was diluted so that the total lipid concentration therein became 0.5 μmol/ml.

(3) Preparation of liposomes III (containing a compound of the invention)

72.4 μmol of L-α-dimyristoyl-phosphatidylcholine, 72.4 μmol of cholesterol, 7.2 μmol of dicetyl phosphate, and 8 or 16 μmol of one of the mannobiose derivatives of the invention as shown below were dissolved in a mixed solvent of chloroform and methanol (volume ratio 2:1) in a test tube with warming. The organic solvent was removed by a nitrogen gas stream to form a lipid film on the glass wall. Then, 6 ml of a solution of 1 mM inulin in PBS (pH 7.4) containing 240 μCi of 3H-inulin was added thereto, and the mixture was shaken and further subjected to mild ultrasonication to prepare a liposome suspension. The suspension was warmed to 40 to 45° C., and extruded through a polycarbonate membrane filter having a pore size of 0.2 μm to prepare a suspension of liposomes having a particle size of 0.2 μm or less. Then, the suspension was subjected to ultracentrifugation (150,000xg, 1 hour, twice), and the supernatant was removed, whereby inulin which had not been encapsulated in the liposomes was removed. PBS (pH 7.4) was added to the residue to obtain a liposome suspension having a total volume of 5.3 ml. Lipid was quantitatively determined by an enzymatic method using a choline group of L-α-dimyristoylphosphatidylcholine as a marker, whereby it was clarified that the suspension contained 10 μmol of lipids as the total lipids per 0.5 ml thereof. The obtained liposomes the used mannobioses and radioactivity are shown below.

| Liposome No. | Mannobiose derivative | Used amount | Radioactivity (μCi/0.5 ml) |
| --- | --- | --- | --- |
| III-1 | Example 3 | 16 μmol | 0.82 |
| III-2 | Example 4 | 16 μmol | 0.95 |
| III-3 | Example 9 | 8 μmol | 0.88 |
| III-4 | Example 9 | 16 μmol | 0.98 |

(4) Preparation of liposomes IV (control)

The same treatment as in the above item (3) was conducted except that 76.2 μmol of L-α-dimyristoyl-phosphatidylcholine, 76.2 μmol of cholesterol and 7.6 μmol of dicetyl phosphate were dissolved in chloroform to obtain a liposome suspension of a total volume of 5.0 ml. The suspension contained 10 μmol of lipids as the total lipids per 0.5 ml thereof, and 1.29 μCi of inulin was encapsulated in the liposomes.

(5) Preparation of 1H-inulin solution (control)

The above PBS (pH 7.4) solution (6 ml) of 1 mM inulin containing 240 μCi of 3H-inulin was diluted 20 times with PBS (pH 7.4) to prepare a solution containing 1 μCi of inulin per 0.5 ml of the diluted solution.

(6) Preparation of liposomes V (control)

The treatment similar to that in the above item (4) was conducted using the same formulation as in the above item (4) to obtain a suspension of liposomes having a total volume of 5.3 ml. The suspension contained 10 μmol of lipids as the total lipids per 0.5 ml thereof, and 1.08 μCi of inulin was encapsulated in the liposomes.

(7) Preparation of liposomes VI (containing a compound of the invention)

The same treatment as in the preparation of liposomes III-2 or III-4 in the above item (3) was conducted using the same formulation as therein to obtain a liposome suspension having a total volume of 4.8 ml. Each of the obtained suspensions contained 10 μmol of lipids as the total lipids per 0.5 ml thereof, and 0.83 or 0.91 μCi of inulin was encapsulated in the liposomes.

TEST 1

A PBS (pH 7.4) solution containing 200 μg/ml of lectin having a sugar specificity to D-mannose (derived from *Vicia fava*, manufactured by Sigma Co.) was prepared. One of the liposome suspensions as obtained in the item (1) (Nos. I-1 to I-5) and the item (2) and the lectin solution were mixed in the ratio of 1:1, mildly shaken and poured into a measuring cell for a spectrophotometer, and absorbance at the wavelength of 450 nm was determined for 30 minutes.

In case of the liposome suspensions formulated with the mannobiose derivatives of the invention prepared in the above item (1), aggregation of liposome was observed by increase of absorbance together with passage of time, and the extent was I-1 ≦I-2 <I-3 =I-4 <I-5. On the other hand, aggregation was not particularly observed in the control liposome (prepared in the above item (2)).

From the foregoing it was confirmed that in the liposomes of the item (1), the mannobiose derivatives of the invention are incorporated into the liposomal membranes and the mannose residues are exposed on the liposomal membrane surfaces, respectively.

TEST 2

The liposome suspensions as obtained in the above item (3) (Nos. III-1 to III-4) and the above item (4) and the 3H-inulin solution as obtained in the above item (5) were intravenously administered to SD strain male rats (body weight 140 to 160 g) at the hind limb in an amount of 0.5 ml portions per 100 g of the body weight, respectively. Thirty minutes later each of the animals was exsanguinated from the carotid artery, the abdomen was opened to excise the liver, lung, kidney and spleen. A part or the whole of each of these organs was homogenized in PBS and determined for radioactivity by a liquid scintillation method to obtain a recovery (%) from each organ based on the dose. The radioactivity recoveries in the serum were calculated estimating the whole blood weight of a rat as 6.5% of the body weight and the serum volume as 50% of the whole blood volume. The results are shown in Table 1. In Table 1, each value represents the average value ± standard error, and each figure in parentheses shows the number of rats. These values are those at 30 minutes after the intravenous injection.

As is apparent from Table 1, distribution of the liposomes containing a mannobiose derivative of the invention to the liver is significantly larger than that of the liposome IV as a control, and it has been confirmed that affinity to the liver is increased in proportion as the containing amount of mannobiose derivative of the invention is increased.

invention to the liver was significantly inhibited by mannan. On the other hand, the control liposome (liposome V) was not affected by mannan.

From the foregoing, it has been confirmed that the liposomes each containing a mannobiose derivative of the invention have an excellent affinity for the Kupffer cells of the liver.

TABLE 2

| | Recovery (%) | | |
|---|---|---|---|
| | Liposome III-2 | Liposome III-4 | Liposome V (control) |
| Non-treated | 34.5 ± 1.7** (3) | 42.1 ± 3.2** (3) | 19.6 ± 2.0 (3) |
| Pre-administration of mannan | 22.8 ± 2.9*** (3) | 24.3 ± 2.1*** (3) | 17.3 ± 3.5 (3) |

**Being significant in 1% level of significance as compared with the control liposome (liposome V).
***Being significant in 1% level of significance as compared with non-treated group.

TEST 4

The liposome suspension as obtained in the above item (7) was intravenously injected into the hind limb of SD strain male rats (body weight 140 to 160 g) in an amount of 0.5 ml per 100 g of the body weight. Thirty minutes later, Nembutal was intraperitoneally administered and the abdomen was opened. Just thereafter, the liver was perfused with a pre-perfusing buffer, a collagenase solution and a Hanks' solution for cell-washing according to the method of Berry-Friend and Seglen to

TABLE 1

| | Recovery % | | | | | |
|---|---|---|---|---|---|---|
| Organ | Liposome III-1 | Liposome III-2 | Liposome III-3 | Liposome III-4 | Liposome IV (control) | $^3$H-inulin solution (control) |
| Liver | 26.6 ± 1.6* (3) | 34.5 ± 1.7** (3) | 28.3 ± 4.1* (3) | 42.1 ± 3.2** (3) | 19.4 ± 2.6 (4) | 1.6 ± 0.2 (3) |
| Lung | 0.50 ± 0.06 (3) | 0.31 ± 0.09 (3) | 0.53 ± 0.11 (3) | 0.62 ± 0.20 (3) | 0.49 ± 0.07 (4) | 0.19 ± 0.08 (3) |
| Kidney | 0.99 ± 0.17 (3) | 0.98 ± 0.20 (3) | 0.85 ± 0.33 (3) | 0.77 ± 0.13 (3) | 0.84 ± 0.26 (4) | 3.64 ± 4.24 (3) |
| Spleen | 4.7 ± 0.8 (3) | 4.0 ± 0.5 (3) | 6.8 ± 1.0 (3) | 7.1 ± 0.7 (3) | 6.2 ± 1.3 (4) | 0.07 ± 0.0 (3) |
| Serum | 11.9 ± 1.9 (3) | 8.0 ± 1.3 (3) | 9.0 ± 1.5 (3) | 11.3 ± 0.8 (3) | 9.9 ± 0.9 (4) | 2.6 ± 1.1 (3) |

*Being significant in 5% level of significance as compared with the control liposome (liposome IV)
**Being significant in 1% level of significance as compared with the control liposome (liposome IV)

TEST 3

By using the liposome suspensions of the above Nos. III-2 to III-4 and the liposome suspension as obtained in the item (6) respectively, inhibition effect by mannan which has D-mannose at the end thereof on affinity to Kupffer cells of the liver was examined. That is, one minute before administration of the liposome suspensions to rats in the same condition as in Test 2, PBS solution of mannan was pre-administered intravenously to the hind limb (the hind limb of the opposite side of liposome injection side), and thereafter the same procedure as in Test 2 was conducted. Dose of mannan was 13.3 mg per 100 g of rat body weight. The results, namely inhibition effects of mannan on distribution of the liposomes to the liver are shown in Table 2. Each value in the table represents the average value ± standard error, and each figure in the parentheses shows the number of rats. These values are those at 30 minutes after the intravenous injection.

As is apparent from Table 2, distribution of the liposomes each containing a mannobiose derivative of the prepare a free liver cells suspension. The suspension was centrifuged under cooling to obtain a fraction containing the liver parenchymal cells and a fraction containing the liver non-parenchymal cells rich in the Kupffer cells of the liver.

Determination of radioactivity of both fractions revealed that 95% or more of radioactivity was recovered from the fraction containing the non-parenchymal cells rich in the Kupffer cells of liver and almost no radioactivity from the fraction containing the liver parenchymal cells.

From the above test, it has been confirmed that the mannobiose derivatives of the invention are useful as a component modifying pharmaceutical preparations, such as liposomes, having a specific affinity for Kupffer cells of liver.

What is claimed is:

1. A mannobiose derivative represented by

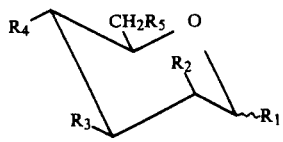

wherein [groups of] $R_1$ to $R_5$ each represents —OH, —OR$_6$, —NHR$_6$, or a group represented by the following formula (a), (b), (c), (d) or (e), provided that one of $R_1$ to $R_5$ represents —OR$_6$ or —NHR$_6$, one of the other 4 groups of $R_1$ to $R_5$ represents one of the groups represented by the formulae (a) to (e), and the remaining 3 groups of $R_1$ to $R_5$ represents —OH and wherein $R_6$ represents an aliphatic acyl group having 12 to 30 carbon atoms:

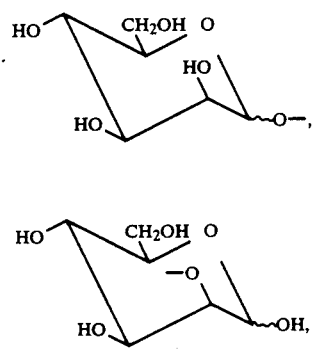

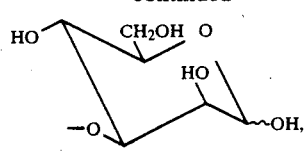

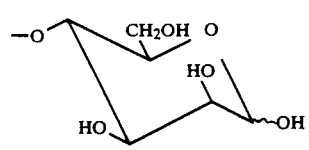

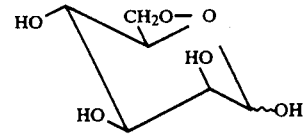

wherein ∼∼∼ represents α or β bond.

2. The derivative of claim 1, wherein one of $R_3$, $R_4$ and $R_5$ is a group represented by the formula (a).

3. The derivative of claim 1, wherein $R_4$ is a group represented by the formula (a), one of $R_1$, $R_2$, $R_3$ and $R_5$ is —NHR$_6$ or —OR$_6$, and the other 3 groups are —OH.

4. The derivative of claim 1, wherein $R_1$ is a group represented by the formula (d), one of $R_2$ to $R_5$ is —NHR$_6$ or —OR$_6$ and the other 3 groups are —OH.

5. The derivative of claim 3, wherein $R_4$ is a group represented by the formula (a), $R_1$ is —OR$_6$ or —NHR$_6$, and $R_2$, $R_3$ and $R_5$ are —OH.

6. The derivative of claim 1, wherein $R_1$, is a group represented by the formula (b), one of $R_2$ to $R_5$ is —NHR$_6$ or —OR$_6$ and the other three groups are —OH.

7. The derivatives of claim 1, wherein $R_2$ is a group represented by the formula (a), one of $R_1$, $R_3$, $R_4$ and $R_5$ is —NHR$_6$ or —OR$_6$ and the other three groups are —OH.

* * * * *